United States Patent
Cheng et al.

(10) Patent No.: US 7,862,908 B2
(45) Date of Patent: Jan. 4, 2011

(54) CONJUGATED COMPOUNDS CONTAINING HYDROINDOLOACRIDINE STRUCTURAL ELEMENTS, AND THEIR USE

(75) Inventors: Chien-Hong Cheng, Hsinchu (TW); Jin-Ju Lin, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 373 days.

(21) Appl. No.: 11/944,635

(22) Filed: Nov. 26, 2007

(65) Prior Publication Data

US 2009/0136779 A1    May 28, 2009

(51) Int. Cl.
*H01L 51/54* (2006.01)
*B32B 9/04* (2006.01)
*C07D 221/18* (2006.01)

(52) U.S. Cl. .................. 428/690; 428/917; 313/504; 313/506; 546/42

(58) Field of Classification Search .............. None
See application file for complete search history.

(56) References Cited

U.S. PATENT DOCUMENTS

| 3,337,545 | A | * | 8/1967 | Zirkle ................. 544/31 |
| 2005/0037232 | A1 | * | 2/2005 | Tyan et al. ............ 428/690 |
| 2007/0247059 | A1 | * | 10/2007 | Cho et al. ............. 313/499 |
| 2008/0303434 | A1 | * | 12/2008 | Cho et al. ............. 313/506 |

FOREIGN PATENT DOCUMENTS

| JP | 5-107784 | * | 4/1993 |
| WO | WO 2006/033563 | * | 3/2006 |

OTHER PUBLICATIONS

Translation for JP 05-107784, which was published Apr. 1993.*

* cited by examiner

*Primary Examiner*—Dawn Garrett
(74) *Attorney, Agent, or Firm*—WPAT, PC; Justin King

(57) ABSTRACT

The present invention discloses a conjugated compound containing a hydroindoloacridine structural element and its applications as a host material or a hole transport material in an organic electronic device. The general structure of the conjugated compound containing a hydroindoloacridine structural element is as follows:

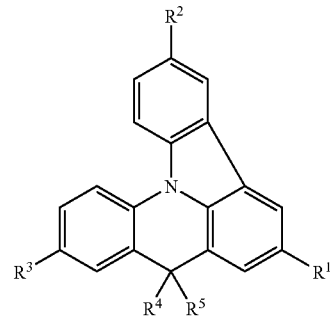

where $R^1 \sim R^5$ can be identical or different.

18 Claims, 4 Drawing Sheets

CONJUGATED COMPOUNDS CONTAINING HYDROINDOLOACRIDINE STRUCTURAL ELEMENTS, AND THEIR USE

BACKGROUND OF THE INVENTION

1. Field of the Invention

The present invention is generally related to a conjugated compound, and more particularly to conjugated compounds containing a hydroindoloacridine structural element and application thereof.

2. Description of the Prior Art

At present, phosphorescent metal complexes have been used as phosphorescent dopants in an organic light emitting diode. Among these metal complexes used in the light-emitting layer of the organic light emitting diode, cyclometallated iridium complexes have been extensively researched since their electron configurations have strong spin-orbit coupling. Since spin-orbit coupling results in mixing between the singlet and triplet excited states, the lifetime of the triplet state is greatly reduced and thereby the phosphorescence efficiency is promoted. In addition, it is found that the doping method can also enhance the efficiency of the device. Therefore, the method of doping phosphorescent substance in a host material is utilized and thus the research in blue phosphorescent host materials becomes important. In the earlier reports, the majority of the blue phosphorescent host materials are carbazoles. Carbazole derivatives have high triplet-state energy and are suitable as the blue phosphorescent host materials. In view of the above matter, developing a novel organic compound having high heat stability and high triplet-state energy to prolong the usage lifetime of the device and to increase luminance efficiency is still an important task for the industry.

SUMMARY OF THE INVENTION

In light of the above background, in order to fulfill the requirements of the industry, the present invention provides a novel conjugated compound containing a hydroindoloacridine structural element and its application as a host material, an electron transport material, or a hole transport material in an organic electronic device.

One object of the present invention is to provide a conjugated compound containing a hydroindoloacridine structural element having high thermal stability to increase the lifetime of an organic electronic device.

Another object of the present invention is to provide a conjugated compound containing a hydroindoloacridine structural element having high triplet-state energy difference, which can not be reached by the common blue phosphorescence host materials, and can be used together with various common phosphorescent materials, such as blue, green, and red phosphorescent materials, like iridium (Ir), platinum (Pt), and osmium (Os) metal complexes. Therefore, this present invention does have the economic advantages for industrial applications.

Accordingly, the present invention discloses a conjugated compound containing a hydroindoloacridine structural element and its applications as a host material, an electron transport material, or a hole transport materials in an organic electronic device. The general structure of the conjugated compound containing hydroindoloacridine structural element is as follows:

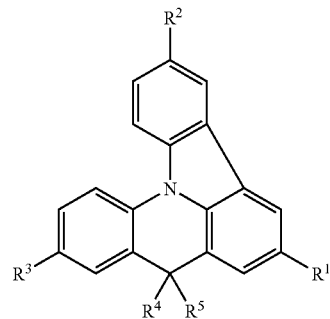

where $R^1 \sim R^5$ can be identical or different.

The invention also discloses the application of the conjugated compound containing a hydroindoloacridine structural element, especially the application as a host material, an electron transport material, and a hole transport material in an organic electroluminescence device or phosphorescence device; or the application as an electron transport material and a hole transport material in other organic electronic devices.

DESCRIPTION OF THE PREFERRED EMBODIMENTS

Figure 1:
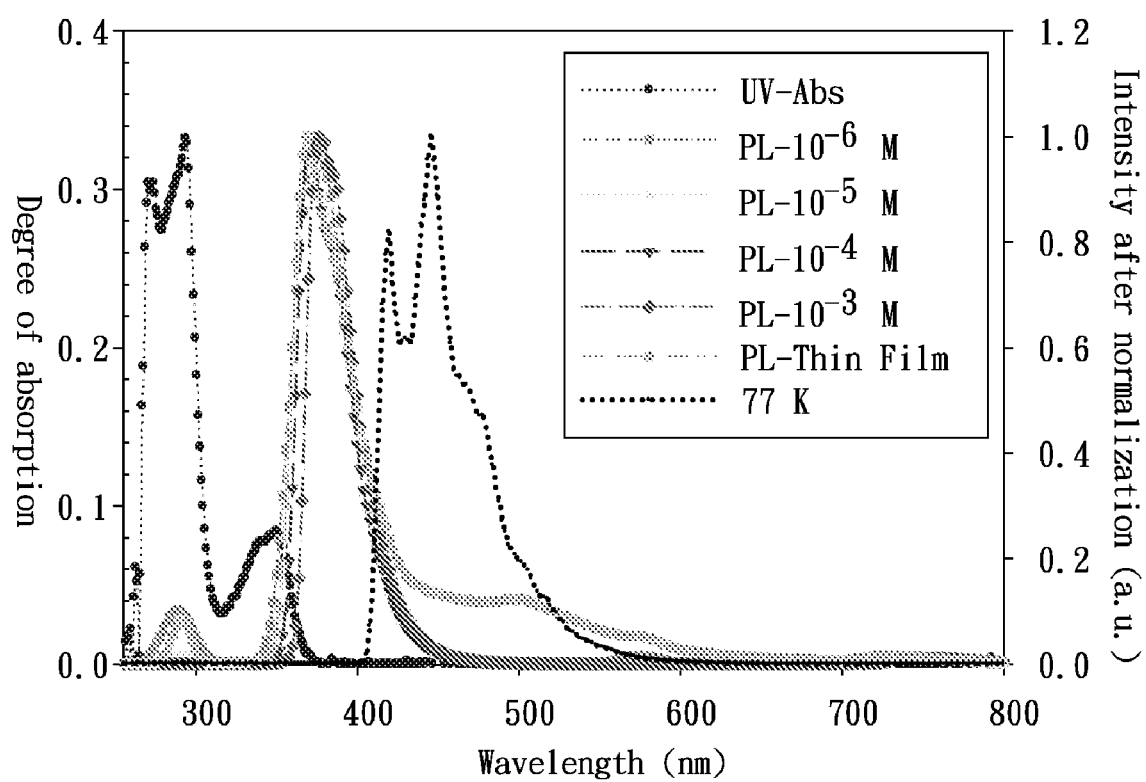
FIG. 1 shows the ultraviolet absorption and emission spectra of DPIA-tBu.

What is probed into the invention is a conjugated compound containing hydroindoloacridine structural element. Detail descriptions of the processes and composition structures will be provided in the following in order to make the invention thoroughly understood. Obviously, the application of the invention is not confined to specific details familiar to those who are skilled in the art. On the other hand, the common processes and composition structures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, a conjugated compound containing hydroindoloacridine structural element is disclosed. The conjugated compound containing hydroindoloacridine structural element has the following general structure:

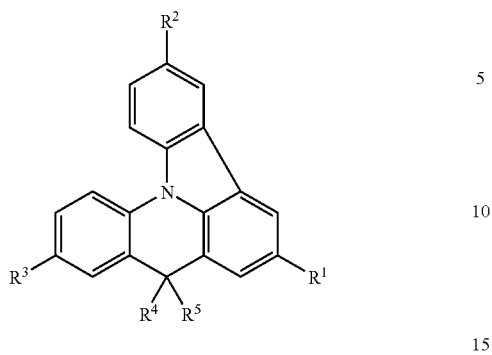

where $R^1 \sim R^5$ can be identical or different and $R^1 \sim R^5$ are independently selected from the group consisting of the following: H atom, halogen substituted aryl group, C1-C20 haloalkyl substituted aryl group, C1-C20 haloalkyl substituted aralkyl group, aryl substituted C1-C20 alkyl group, C1-C20 alkyl group (such as methyl, ethyl, butyl, cyclohexyl, etc.), C1-C20 alkoxy group, amino group, aryl substituted amino group, C1-C20 alkyl substituted amino group, nitrile group, nitro group, carbonyl group, cyano group (—CN), substituted aromatic amino group, phosphoryl (P=O) aryl group, Si-containing aryl group, and heterocyclic ring group. In addition, $R^4$ and $R^5$ are not H atoms simultaneously.

The aryl group comprises phenyl, naphthyl, diphenyl, anthryl, pyrenyl, phenanthryl, fluorene, or other multi-phenyl group. The heterocyclic ring group can be pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, phenanthroline, or other heterocyclic aryl group.

The preferred examples of the structure and fabricating method for the conjugated compound containing hydroindoloacridine structural element according to the invention are described in the following. However, the scope of the invention should be based on the claims, but is not restricted by the following examples.

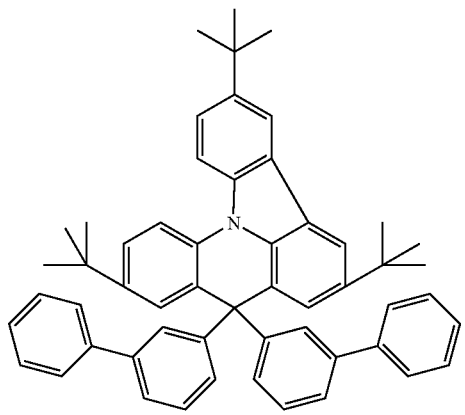

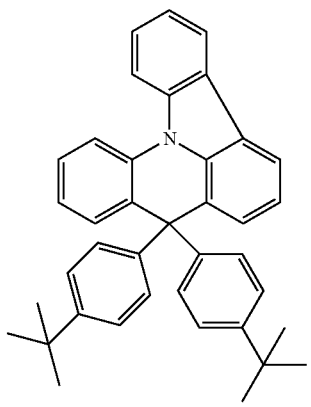

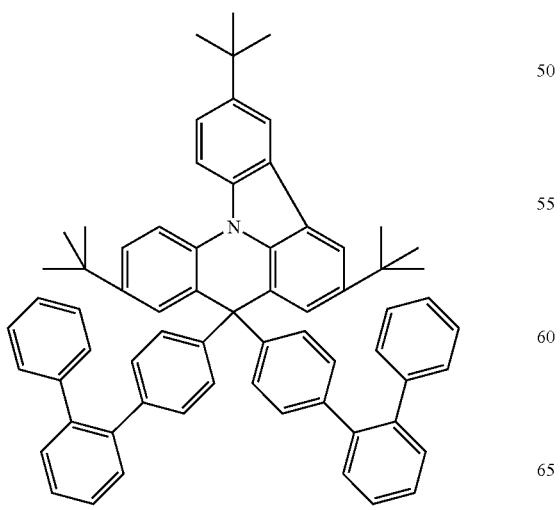

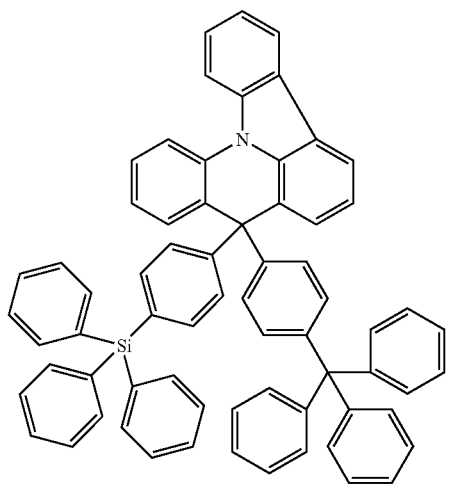

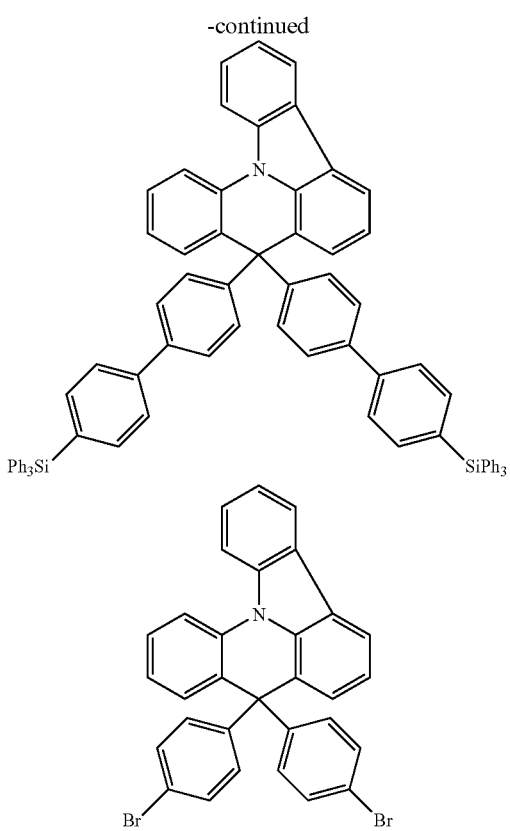

Example 1

Method for Forming a Conjugated Compound Containing Hydroindoloacridine Structural Element At first, the compound F-01 (10 mmole), carbazole (10 mmole), potassium carbonate (100 mmole), sodium sulfate (100 mmole), and copper powder (1 mmole) are placed in a reaction flask and then nitrobenzene (20 mL) is added. At the refluxing temperature, the mixture is heated and stirred for 24 hrs. After the reaction is finished, the nitrobenzene is removed by reduced pressure distillation. The residual mixture is extracted by water and methylene chloride and then the organic layer is collected. After water is removed from the organic layer by salting out, concentration is carried out to obtain the compound F-02, as shown in Scheme 1.

Scheme 1

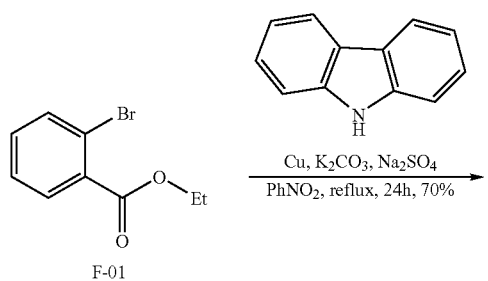

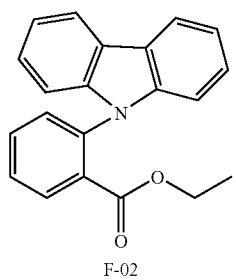

Next, in a reaction flask, the compound F-02 (10 mmole) is dissolved in THF (50 mL) and a lithium reagent or Grignard reagent (20 mmole) is added. In the nitrogen environment, the reaction is carried out for 18 hrs. After the reaction is finished, ammonium chloride saturated solution is added to terminate the reaction. The extraction by ethyl acetate is carried out. After water is removed from the organic layer by salting out, the solvent is removed and acetic acid (10 mL) and concentrated hydrochloric acid (1 mL) are added. At the refluxing temperature, the reaction is taken place, as show in Scheme 2. After the reaction is finished, sodium carbonate saturated solution is added to neutralize acetic acid and hydrochloric acid. As the solution becomes weak acidic, suction filtration is carried out and solids are collected. Then, ethanol is used to carry out recrystallization. Thus, a conjugated compound containing hydroindoloacridine structural element is obtained.

Scheme 2

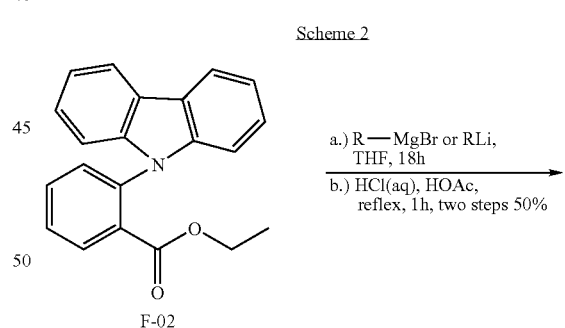

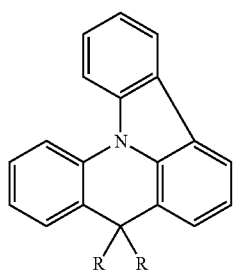

Example 2

8,8-Bis-(4-tert-butyl-phenyl)-8H-indolo[3,2,1-de]acridine (hereinafter abbreviated as DPIA-tBu)

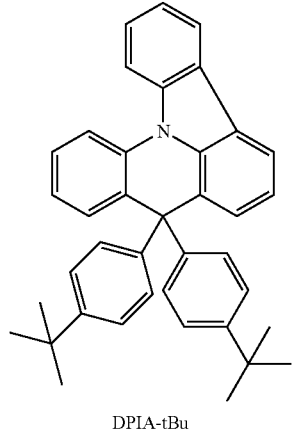

DPIA-tBu $^1$H NMR (400 M Hz, CDCl$_3$): δ 1.23 (s, 18H), 6.94 (d, J=8.4 Hz, 4H), 7.04-7.08 (m, 3H), 7.20 (d, J=8.4 Hz, 4H), 7.29-7.38 (m, 3H), 7.51 (t, J=8 Hz, 1H), 7.91 (d, J=7.6 Hz, 1H), 8.10 (t, J=7.2 Hz, 3H) $^{13}$C NMR (100 M Hz, CDCl$_3$): δ 31.3 (CH$_3$), 34.3 (C), 56.3 (C), 113.3 (CH), 114.4 (CH), 117.9 (CH), 121.0 (CH), 121.1 (CH), 121.8 (C), 122.1 (CH), 122.6 (CH), 124.5 (CH), 126.1 (CH), 126.3 (CH), 126.8 (C), 127.3 (CH), 128.3 (C), 129.7 (CH), 132.0 (CH), 132.5 (C), 136.9 (C), 137.6 (C), 138.6 (C), 143.3 (C), 149.0 (C). HRMS (EI, m/z): calcd for C$_{39}$H$_{37}$N 519.2926, found 519.2913 (M$^+$) Anal. Calcd. for C$_{39}$H$_{37}$N: C, 90.13; H, 7.18; N, 2.70%. Found: C, 89.98; H, 7.09; N, 2.66%. (The ultraviolet absorption and emission spectra of DPIA-tBu is shown in FIG. 1.)

Example 3

8,8-Bis-(4-triphenylsilanyl-phenyl)-8H-indolo[3,2,1-de]acridine (hereinafter abbreviated as DPIA-BS)

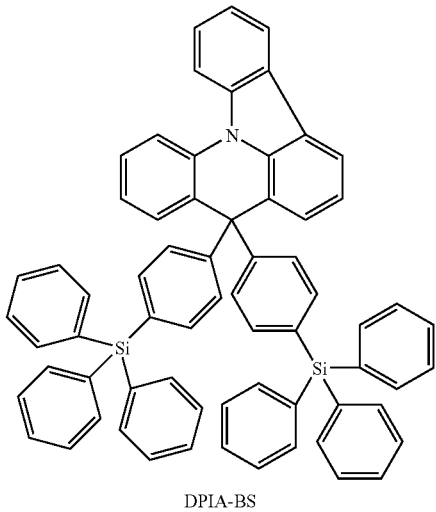

Figure 2:
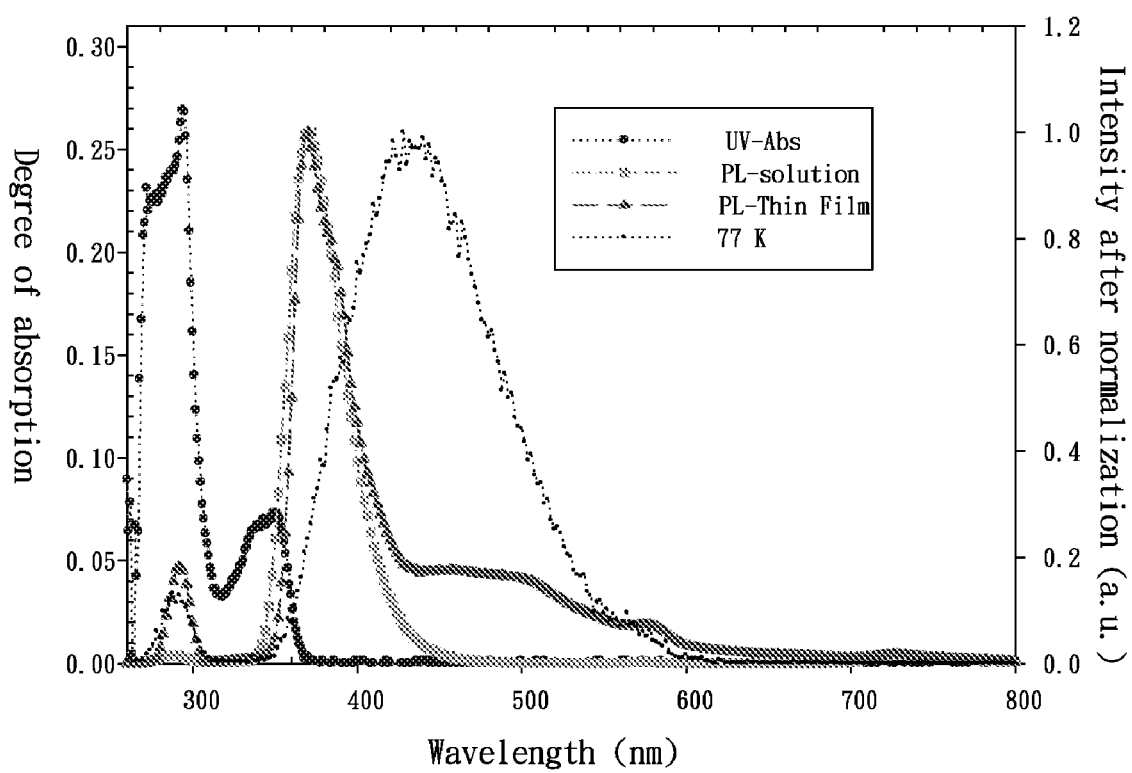
FIG. 2 shows the ultraviolet absorption and emission spectra of DPIA-BS.

DPIA-BS $^1$H NMR (600 M Hz, CD$_2$Cl$_2$): δ 7.05-7.13 (m, 8H), 7.33-7.44 (m, 22 H), 7.52-7.56 (m, 13H), 7.96 (d, J=8.0 Hz, 2H), 8.14 (t, J=8.0 Hz, 4H). Anal. Calcd. for C$_{67}$H$_{49}$NSi$_2$: C, 87.06; H, 5.34; N, 1.52%. Found: C, 86.68; H, 5.36; N, 1.53% (The ultraviolet absorption and emission spectra of DPIA-BS is shown in FIG. 2.)

Example 4

8,8-Bis-(4-bromo-phenyl)-8H-indolo[3,2,1-de]acridine (hereinafter abbreviated as DPIA-Br)

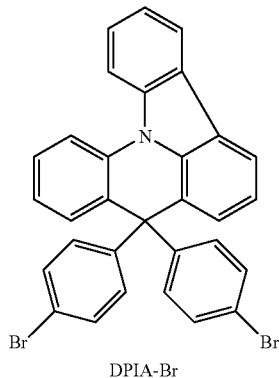

DPIA-Br $^1$H NMR (400 M Hz, CDCl$_3$): δ 6.90 (d, J=8.0 Hz, 4H), 6.97 (d, J=8.0 Hz, 1H), 7.00 (d, J=8.0 Hz, 1H), 7.09 (t, J=7.2 Hz, 1H), 7.30-7.41 (m, 7H), 7.53 (t, J=8.0 Hz, 1H), 7.93 (d, J=8.0 Hz, 1H), 8.07 (d, J=8.0 Hz, 1H), 8.11 (d, J=8.0 Hz, 2H). $^{13}$C NMR (100 M Hz, CDCl$_3$): δ 56.4 (C), 110.0 (C), 113.6 (CH), 114.4 (CH), 118.6 (CH), 120.9 (C), 121.2 (CH), 121.4 (CH), 122.1 (C), 122.4 (CH), 122.9 (CH), 125.8 (CH), 126.5 (CH), 126.6 (C), 126.8 (C), 127.9 (CH), 131.0 (CH, C), 131.5 (CH), 131.8 (CH), 136.8 (C), 137.3 (C), 138.6 (C), 144.7 (C) HRMS (EI, m/z): calcd for C$_{31}$H$_{19}$Br$_2$N 562.9884 found 562.9888 (M$^+$).

Example 5

8,8-Bis-(4'-triphenylsilanyl-biphenyl-4-yl)-8H-indolo[3,2,1-de]acridine (hereinafter abbreviated as DPIA-BSP)

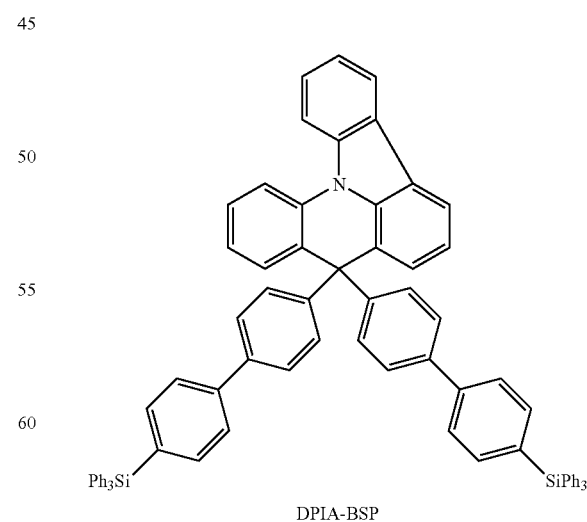

Figure 3:
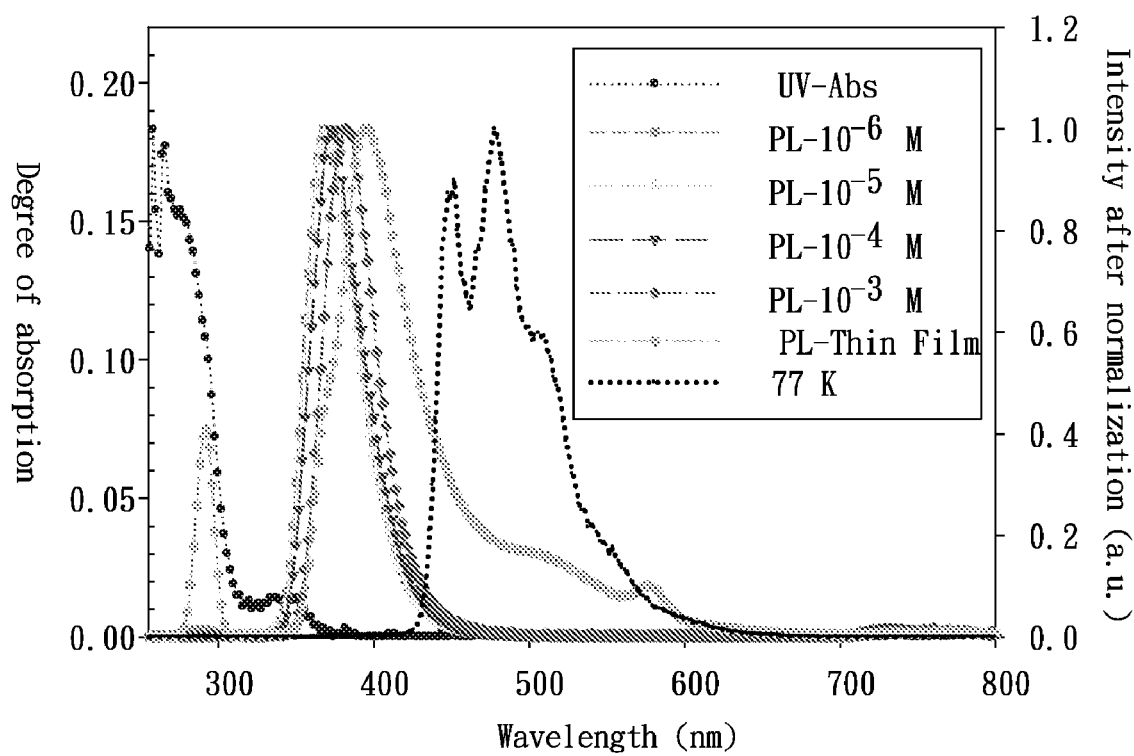
FIG. 3 shows the ultraviolet absorption and emission spectra of DPIA-BSP.
Figure 4:
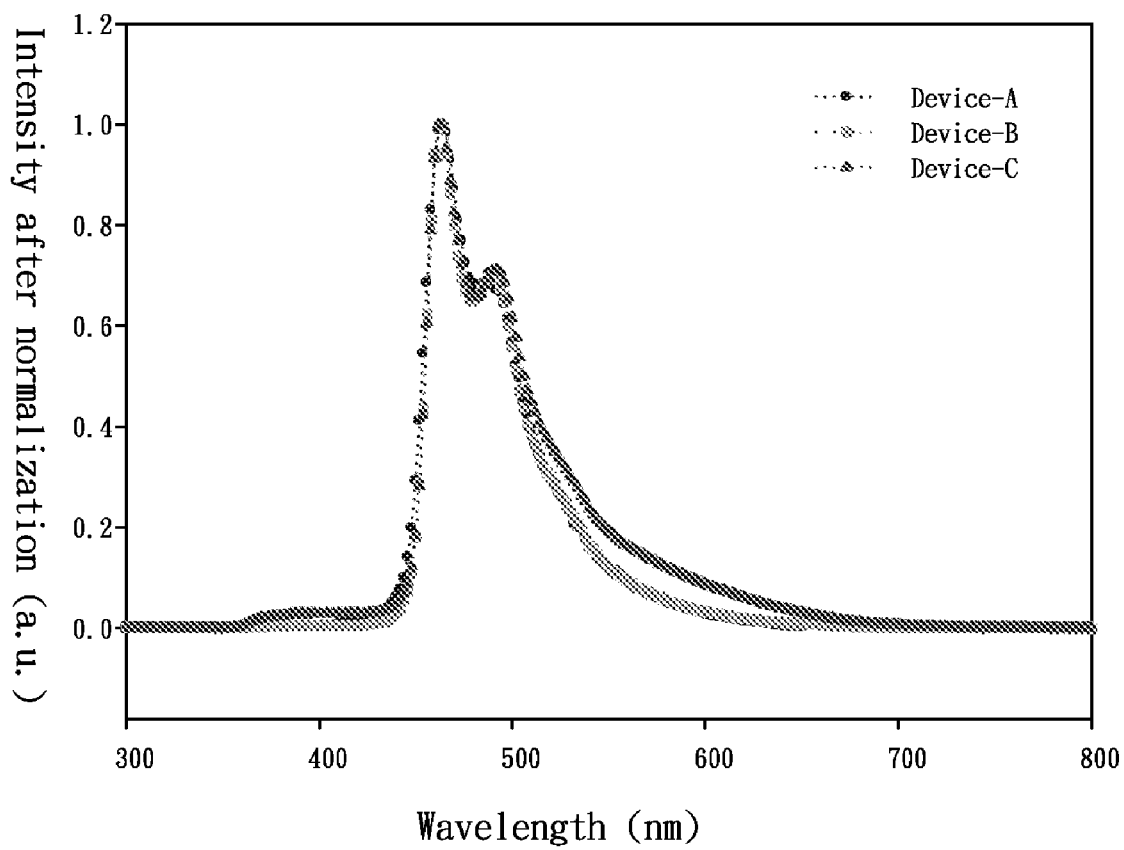
FIG. 4 shows the emission spectra of the devices A~C according to the invention.

DPIA-BSP $^1$H NMR (400 M Hz, CDCl$_3$): δ 7.12-7.22 (m, 7H), 7.33-7.65 (m, 46 H), 7.97 (d, J=8.0 Hz, 1H), 7.09 (t, J=7.2 Hz, 1H), 8.11-8.19 (m, 3H). $^{13}$C NMR (100 MHz, CDCl$_3$): δ 56.7 (C), 113.5 (CH), 114.5 (CH), 118.3 (CH), 121.2 (CH), 121.3 (CH), 122.1 (C), 122.3 (CH), 122.8 (CH), 126.2 (CH), 126.4 (CH), 126.5 (CH), 126.8 (CH), 127.7 (CH, C), 127.9 (CH), 128.0 (C), 129.6 (CH), 130.6 (CH), 131.9 (CH), 132.0 (C), 133.0 (C), 134.2 (C), 136.4 (CH), 136.8 (CH), 137.0 (C), 137.6 (C), 138.6 (C), 138.9 (C), 141.5 (C), 145.5 (C). HRMS (FAB, m/z): calcd for C$_{79}$H$_{57}$Si$_2$N 1075.4030 found 1076.4111 (M$^+$+1) Anal. Calcd. for C$_{79}$H$_{57}$Si$_2$N: C, 88.14; H, 5.34; N, 1.30%. Found: C, 88.03; H, 5.21; N, 1.25%. ○ (The ultraviolet absorption and emission spectra of DPIA-BSP is shown in FIG. 3.)

According to this embodiment, the conjugated compound containing hydroindoloacridine structural element has excellent heat stability and high triplet-state energy difference. Therefore, as the conjugated compound containing hydroindoloacridine structural element is applied in an organic electronic device, the excellent heat stability makes the lifetime of the organic electronic device increased. Furthermore, as the conjugated compound containing hydroindoloacridine structural element is applied in an organic light emitting device, the conjugated compound containing hydroindoloacridine structural element has high triplet-state energy difference, which can not be provided by the existing known blue phosphorescence host materials, and can be used together with various common phosphorescent materials, such as blue, green, and red phosphorescent materials, like iridium (Ir), platinum (Pt), and osmium (Os) metal complexes. Furthermore, by doped with various common phosphorescent materials, such as blue, green, and red phosphorescent materials, like iridium (Ir), platinum (Pt), and osmium (Os) metal complexes, the wavelength irradiated from the light-emitting layer can be adjusted according to actual needs.

In this embodiment, the conjugated compound containing hydroindoloacridine structural element can be applied in an organic electroluminescence and/or phosphorescence device, especially used as a host material or a hole transport material. The conjugated compound containing hydroindoloacridine structural element can also be applied as a hole transport material in other organic electronic device. The organic electronic device can be a solar cell, an organic thin film transistor, an organic photoconductor, or other organic semiconducting device well-known to those who are skilled in the art.

In a second embodiment of the invention, an organic light emitting device is disclosed. Generally, the color of light emitted by the organic light emitting device is determined by the fluorescent organic material in the device. Therefore, by doping small amount of guest emitters with high luminance efficiency in host emitters, the recombination efficiency of carriers can be increased. These guest emitters have smaller energy gap, higher luminance efficiency, and shorter recombination lifetime than the host emitters. Therefore, the excitons of the host emitters quickly transfer to the guest emitters through energy transition to carry out recombination effectively. Besides increasing luminance efficiency, the color of the emitted light covers the whole visible light region.

Generally, guest emitters are used together with host emitters by co-evaporation or dispersion, or by spin coating. Guest emitters receive energy from the excited host emitters through energy transfer or carrier trap to produce different colors, such as red, green, and blue, and to increase luminance efficiency. Besides the above mentioned fluorescence guest emitters, new development in phosphorescence material is also researched. As an organic molecule is excited, one quarter of excited electrons form asymmetric spin singlet state and release energy through fluorescence. However, three quarters of excited electrons form symmetric spin triplet state but do not release energy through radiated phosphorescence to thereby lose efficiency. At present, the material capable of releasing the triplet-state energy of the excited electrons through radiated phosphorescence usually is an organic metallic compound having a center transition metal, such as osmium (Os), iridium (Ir), platinum (Pt), europium (Eu), ruthenium (Ru), etc., and the ligand of the organic metallic compound is a nitrogen-containing heterocyclic compound.

According to this embodiment, the organic light emitting device comprises a pair of electrodes and at least one organic layer provided between the electrodes. The at least one organic layer comprises one light-emitting layer and at least one of the organic layers comprises one conjugated compound containing hydroindoloacridine structural element, having the following general structure:

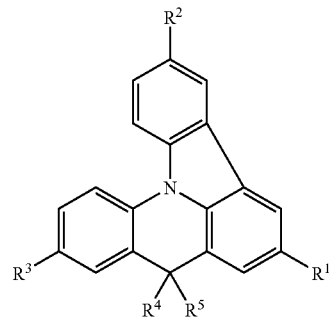

where R$^1$~R$^5$ can be identical or different and R$^1$~R$^5$ are independently selected from the group consisting of the following: H atom, halogen substituted aryl group, C1-C20 haloalkyl substituted aryl group, C1-C20 haloalkyl substituted aralkyl group, aryl substituted C1-C20 alkyl group, C1-C20 alkyl group (such as methyl, ethyl, butyl, cyclohexyl, etc.), C1-C20 alkoxy group, amino group, aryl substituted amino group, C1-C20 alkyl substituted amino group, nitrile group, nitro group, carbonyl group, cyano group (—CN), substituted aromatic amino group, phosphoryl (P═O) aryl group, Si-containing aryl group, and heterocyclic ring group. In addition, R$^4$ and R$^5$ are not H atoms simultaneously.

The aryl group comprises phenyl, naphthyl, diphenyl, anthryl, pyrenyl, phenanthryl, fluorene, or other multi-phenyl group. The heterocyclic ring group can be pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, phenanthroline, or other heterocyclic aryl group.

In a preferred example of this embodiment, the conjugated compound containing hydroindoloacridine structural element is applied in the light-emitting layer of the organic light emitting device. According to another preferred example of this embodiment, the conjugated compound containing hydroindoloacridine structural element is applied as a host material in the light-emitting layer of the organic light emitting device. The light-emitting layer can further comprise a guest emitting material and the guest emitting material comprises a transition metal complex. The transition metal of the transition metal complex can be selected from the group consisting of the following: iridium (Ir), platinum (Pt), osmium (Os), copper (Cu), rhodium (Rh), europium (Eu), and ruthenium (Ru). The guest emitting material can be a blue, green, or red phosphorescence material. According to another preferred example of this embodiment, the conjugated compound containing hydroindoloacridine structural element can be applied in the hole transport layer of the organic light emitting device. According to another preferred example of this embodiment, the conjugated compound containing hydroindoloacridine structural element can be applied in the electron transport layer of the organic light emitting device.

General Process for Fabricating an Organic Light Emitting Device

An ITO glass with etched circuitry is placed in a cleaning liquid (neutral cleanser:deionized water=1:50) and carried out supersonic oscillation for 5 minutes. Then, the ITO glass is brushed by a soft brush and sequentially carried out the following steps: placing in 50 mL of deionized water, oscillating in electronic grade acetone for 5 minutes, and drying by nitrogen. The cleaned ITO glass is placed in an ultraviolet-ozone machine for 5 minutes. Finally, the ITO glass with the ITO surface facing downward is provided on the substrate holder in an evaporator. The chamber of the evaporator is then vacuumed. The process of evaporating thin film does not start until the pressure in the chamber reaches $5 \times 10^{-6}$ torr. The conditions of evaporation are as follows. The evaporation rate for the organic films is controlled at 1~2 Å/s and then the expected organic films are evaporated sequentially. The evaporation rate of magnesium for the metal film is 5 Å/s while that of silver is 0.5 Å/s (Mg:Ag=10:1). The Mg—Ag co-evaporated metal film has a thickness of 55 nm. Finally, a silver layer having a thickness of 100 nm as a protection layer is formed. In the case of choosing LiF/Al system as metal, firstly LiF is evaporated with a rate of 0.1 Å/s to form a film with a thickness of 1 nm and secondly an aluminum layer having a thickness of 100 nm as a protection layer is formed.

During the process of evaporation, the rotational speed of the device is about 20 rpm. After the evaporation process is finished, the metal electrode is kept to cool for 20 minutes and then the chamber is filled with nitrogen until the pressure returns normal pressure.

On the other hand, after the OLED device is fabricated, the EL spectra and CIE coordination of the device are measured by Hitachi F-4500 spectra scan spectrometer. In addition, the properties, such as current, voltage, and brightness of the device are measured by Kiethley 2400 programmable voltage-current source. The measurements are carried out at room temperature (about 25° C.) and 1 atm.

Example 6

By the general process of fabricating OLED, DPIA-tBu, DPIA-BS, DPIA-Br, and DPIA-BSP are used as the host materials and OLEDs are fabricated by doping a blue phosphorescence material in the host emitting materials. The blue phosphorescence material is shown in the following.

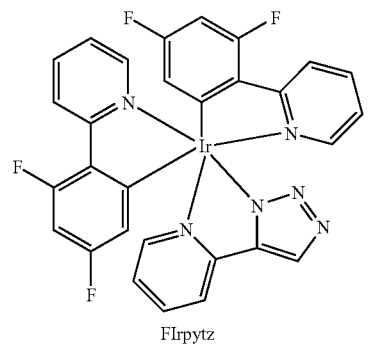

FIrpytz

The structure of each device according to this example is shown in the following:

Device A: NPB(30 nm)/DPIA-tBu:6% FIrpytz(30 nm)/BCP (10 nm)/Alq(30 nm);

Device B: TCTA(30 nm)/DPIA-tBu:6% FIrpytz(30 nm)/BCP (10 nm)/Alq(30 nm); and

Device C: TCTA(30 nm)/DPIA-BS:6% FIrpytz(30 nm)/BCP (10 nm)/Alq(30 nm).

The optical properties and efficiency of the devices A~C are measured and shown in Table 1.

TABLE 1

| Device | Threshold voltage (V) | Maximum external quantum efficiency (%, V) | Brightness (at 100 mA/m$^2$) (cd/m$^2$) | Current efficiency (cd/A, V) | Maximum efficiency (lm/W, V) | CIE coordinate (x, y) at 10 V |
|---|---|---|---|---|---|---|
| A | 3.9 | 7.45, 6.5 | 5930, 10.4 | 12.53, 6.5 | 6.06, 6.5 | 0.15, 0.24 |
| B | 5.9 | 7.76, 9.5 | 6171, 13.1 | 13.45, 9.5 | 4.52, 9.0 | 0.15, 0.25 |
| C | 4.8 | 2.04, 9.0 | 2099, 11.9 | 3.67, 9.0 | 1.28, 9.0 | 0.19, 0.29 |

As shown in the Table 1, the conjugated compound containing hydroindoloacridine structural element according to the invention can be used as the phosphorescent host material and applied in the organic light emitting diode. Referring to Table 1 and FIG. 1, the devices A~C emit blue phosphorescence and have high brightness, high current efficiency, and excellent CIE coordinate.

In this embodiment, the conjugated compound containing hydroindoloacridine structural element is applied as a host material or a hole transport material in an organic electroluminescence device. On the other hand, the conjugated compound containing hydroindoloacridine structural element has the electron and hole transport characteristics to be applied as an electron transport material or a hole transport material in other electronic devices, besides in an organic electroluminescence device According to the invention, the conjugated compound containing hydroindoloacridine structural element has the excellent heat stability. As applied in an organic electronic device, the conjugated compound containing hydroindoloacridine structural element has the excellent heat stability to make the lifetime of the organic electronic device effectively increased. In addition, the conjugated compound containing hydroindoloacridine structural element has high triplet-state energy difference. As applied in an organic light emitting device, the conjugated compound containing hydroindoloacridine structural element provides high triplet-state energy difference, which can not be provided by various common blue, green, red phosphorescent host materials, and can be used together with various common phosphorescent materials, such as the iridium (Ir), platinum (Pt), and osmium (Os) metal complexes. Therefore, this present invention does have the economic advantages for industrial applications.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A conjugated compound containing a hydroindoloacridine structural element, comprising the following general structure:

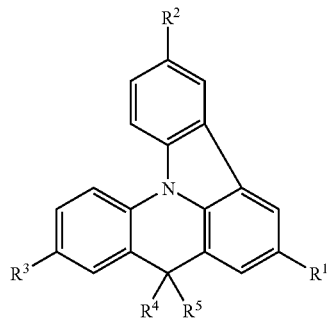

wherein $R^1 \sim R^5$ can be identical or different and $R^1 \sim R^3$ are independently selected from the group consisting of the following: H atom, halogen substituted aryl group, C1-C20 haloalkyl substituted aryl group, C1-C20 haloalkyl substituted aralkyl group, aryl substituted C1-C20 alkyl group, C1-C20 alkyl group, C1-C20 alkoxy group, nitrile group, nitro group, carbonyl group, cyano group (—CN), phosphoryl (P═O) aryl group, Si-containing aryl group, and heterocyclic ring group; wherein $R^4 \sim R^5$ are independently selected from the group consisting of the following: halogen substituted aryl group, C1-C20 haloalkyl substituted aryl group, C1-C20 haloalkyl substituted aralkyl group, amino group, aryl substituted amino group, C1-C20 alkyl substituted amino group, nitrile group, nitro group, carbonyl group, cyano group (—CN), substituted aromatic amino group, phosphoryl (P═O) aryl group, Si-containing aryl group, and heterocyclic ring group.

2. The conjugated compound according to claim 1, wherein each of said aryl group is selected from the group consisting of the following: phenyl, naphthyl, diphenyl, anthryl, pyrenyl, phenanthryl, and fluorene.

3. The conjugated compound according to claim 1, wherein said heterocyclic ring group is selected from the group consisting of the following: pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, and phenanthroline.

4. The conjugated compound according to claim 1, wherein said conjugated compound containing a hydroindoloacridine structural element is utilized in an organic electroluminescence and/or phosphorescence device.

5. The conjugated compound according to claim 1, wherein said conjugated compound containing a hydroindoloacridine structural element is utilized as a host material for an organic electroluminescence and/or phosphorescence device.

6. The conjugated compound according to claim 1, wherein said conjugated compound containing a hydroindoloacridine structural element is utilized as a hole transport material for an organic electronic device.

7. An organic light emitting device, comprising:
a pair of electrodes; and
at least one organic layer provided between said electrodes;
wherein said at least one organic layer comprises one light-emitting layer and at least one of said organic layers comprises one conjugated compound containing a hydroindoloacridine structural element, having the following general structure:

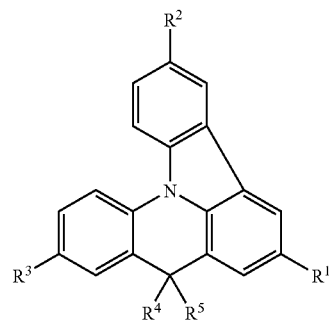

wherein $R^1 \sim R^5$ can be identical or different and $R^1 \sim R^3$ are independently selected from the group consisting of the following: H atom, halogen substituted aryl group, C1-C20 haloalkyl substituted aryl group, C1-C20 haloalkyl substituted aralkyl group, aryl substituted C1-C20 alkyl group, C1-C20 alkyl group, C1-C20 alkoxy group, nitrile group, nitro group, carbonyl group, cyano group (—CN), substituted aromatic amino group, phosphoryl (P═O) aryl group, Si-containing aryl group, and heterocyclic ring group; wherein $R^4 \sim R^5$ are independently selected from the group consisting of the following: halogen substituted aryl group, C1-C20 haloalkyl substituted aryl group, C1-C20 haloalkyl substituted aralkyl group, amino group, aryl substituted amino group, C1-C20 alkyl substituted amino group, nitrile group, nitro group, carbonyl group, cyano group (—CN), substituted aromatic amino group, phosphoryl (P=O) aryl group, Si-containing aryl group, and heterocyclic ring group.

8. The device according to claim 7, wherein each of said aryl group is selected from the group consisting of the following: phenyl, naphthyl, diphenyl, anthryl, pyrenyl, phenanthryl, and fluorene.

9. The device according to claim 7, wherein said heterocyclic ring group is selected from the group consisting of the following: pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, 1,2,3,4-tetraazole, and phenanthroline.

10. The device according to claim 7, wherein said conjugated compound containing a hydroindoloacridine structural element is utilized in said light-emitting layer of said organic light emitting device.

11. The device according to claim 7, wherein said conjugated compound containing a hydroindoloacridine structural element is utilized as a host material in said light-emitting layer of said organic light emitting device.

12. The device according to claim 7, wherein said conjugated compound containing a hydroindoloacridine structural element is utilized as an electron transport material of said organic light emitting device.

13. The device according to claim 7, wherein said conjugated compound containing a hydroindoloacridine structural element is utilized as a hole transport material of said organic light emitting device.

14. The device according to claim 7, wherein said light-emitting layer further comprises a guest emitting material and said guest emitting material comprises a transition metal complex.

15. The device according to claim 14, wherein the transition metal of said transition metal complex is selected from the group consisting of the following: iridium (Ir), platinum (Pt), osmium (Os), copper (Cu), rhodium (Rh), europium (Eu), and ruthenium (Ru).

16. The device according to claim 14, wherein said guest emitting material is blue phosphorescent.

17. The device according to claim 14, wherein said guest emitting material is green phosphorescent.

18. The device according to claim 14, wherein said guest emitting material is red phosphorescent.

* * * * *